United States Patent [19]

Nanataki et al.

[11] Patent Number: 5,419,827
[45] Date of Patent: May 30, 1995

[54] PARTIALLY STABILIZED ZIRCONIA AND ITS APPLICATION TO ELECTRONICAL DEVICE

[75] Inventors: Tsutomu Nanataki; Kazuyoshi Shibata, both of Nagoya, Japan

[73] Assignee: NGK Insulators, Ltd., Nagoya, Japan

[21] Appl. No.: 887,810

[22] Filed: May 26, 1992

[30] Foreign Application Priority Data

May 29, 1991 [JP] Japan .................... 3-154148

[51] Int. Cl.⁶ .................... G01N 27/26; C04B 35/48
[52] U.S. Cl. .................... 204/421; 204/424; 204/426; 501/104
[58] Field of Search ............ 501/104; 204/421, 424, 204/426

[56] References Cited

U.S. PATENT DOCUMENTS

| | | | |
|---|---|---|---|
| 4,181,579 | 1/1980 | Booth | 204/421 |
| 4,183,798 | 1/1980 | Esper et al. | 204/421 |
| 4,820,667 | 4/1989 | Tsunekawa et al. | 501/104 |
| 5,008,221 | 4/1991 | Ketcham | 501/104 |

OTHER PUBLICATIONS

"Zirconia Ceramics" Uchida-Roukakuho: Tokyo: 1989: pp. 221-230 No month available.

Primary Examiner—John Niebling
Assistant Examiner—Bruce F. Bell
Attorney, Agent, or Firm—Adduci, Mastriani, Schaumberg & Schill

[57] ABSTRACT

Partially stabilized zirconia is disclosed which contains yttrium oxide; an MgO ingredient in the grain boundaries; and the remainder being zirconium oxide and unavoidable impurities. Preferably a critical temperature difference of the partially stabilized zirconia is larger than or equal to 340° C.

The partially stabilized zirconia may be suitably used as a solid electrolyte body in an electrochemical device with at least a pair of electrodes.

An MgO ingredient and, preferably an $Al_2O_3$ and a $SiO_2$ ingredients as well are believed to be present in the grain boundary in the partially stabilized zirconia and responsible for excellent thermal shock resistance.

14 Claims, 1 Drawing Sheet

PARTIALLY STABILIZED ZIRCONIA AND ITS APPLICATION TO ELECTRONICAL DEVICE

BACKGROUND OF THE INVENTION AND DESCRIPTION OF THE PRIOR ART

This invention relates to partially stabilized zirconia and its application to an electrochemical device. It is especially related to partially stabilized zirconia containing yttrium oxide with improved thermal shock resistance and its application to an electrochemical sensor.

During a cooling process after firing in its preparation, zirconia has been known to undergo a phase transition from a cubic system in high temperatures to a tetragonal system and another phase transition from the tetragonal system to a monoclinic system, which is stable at room temperature. A significant volume change is involved in the phase transition from the tetragonal system to the monoclinic system or vice versa, and this volume change tends to lead to cracks in a fired body of zirconia.

Partially stabilized zirconia containing a stabilizer such as yttrium oxide, magnesium oxide, calcium oxide, etc. has been developed to stabilize a cubic phase and/or a tetragonal phase in zirconia such that these phases are maintained as meta-stable phases down to room temperature without the phase transition to the monoclinic system. Such partially stabilized zirconia has been well known to possess high mechanical strength and strong toughness.

Due to its application to various fields such as heat resistant materials and members, solid electrolyte bodies, etc., partially stabilized zirconia is required to possess not only satisfactory mechanical strength but also satisfactory thermal shock resistance at high temperatures.

Partially stabilized zirconia, however, has not yet attained satisfactory thermal shock resistance. Thermal shock resistance can be parameterized by a critical temperature difference beyond which a sample breaks or cracks because of a sudden temperature change. Usually this bearable limit of a sudden temperature change is tested by quenching a hot sample by immersing it in water at room temperature. For example, according to Somiya; Yoshimura "Zirconia Ceramics" Uchida-Roukakuho:Tokyo; 1989; pp 221–230, partially stabilized zirconia, mainly composed of grains belonging to a cubic system, which contains 6% by mole of yttrium oxide, has a critical temperature difference of 200° C., and partially stabilized zirconia, mainly composed of a tetragonal system, which contains 2 to 3% by mole of yttrium oxide, has a critical temperature difference of 250° C. to 275° C. These values are not large enough in many applications of partially stabilized zirconia.

There has not been much research on improving thermal shock resistance of partially stabilized zirconia with notable results. One of the examples is found in "International Symposium on Science and Technology of Sintering", Fourth Ed.: Tokyo; 1988; pp 1155–1160. This example has provided a method of obtaining partially stabilized zirconia containing 20% by volume of alumina and another method of obtaining partially stabilized zirconia containing 10% by volume of mullite. Additionally, a method has been disclosed in Japanese Patent Laid-Open No. 56-41873 of obtaining zirconia which is mainly composed of grains belonging to a cubic system and which contains 0.5 to 4.5% by weight of grains of a monoclinic system.

None of the three methods is satisfactory. The method of obtaining partially stabilized zirconia containing 20% by volume of alumina, requires temperatures higher than 1600° C. in firing or an HIP treatment because a considerable amount of alumina is added. This temperature requirement leads to a higher cost and limitations in its application. Moreover, firing at such high temperatures may help grains belonging to a tetragonal system grow to result in decreased thermal stability of a product. Furthermore, a large content of alumina may lead to a product without satisfactory oxygen ion conductivity when applied to a solid electrolyte body.

Similarly, the method of obtaining partially stabilized zirconia containing 10% by volume of mullite, has all the disadvantages mentioned above. Moreover, mechanical strength of the zirconia worsens due to incorporation of so much mullite.

Finally the method disclosed in Japanese Patent Laid-Open No. 41873 (1981), includes a step of providing heat hysteresis by carefully controlling temperatures during and after firing, and is useful in obtaining partially stabilized zirconia containing $Y_2O_3$, CaO, and MgO with high thermal shock resistance and durability for long usage.

However, the critical temperature difference of this improved partially stabilized zirconia is still about 250° C., and its bending strength is half that of partially stabilized zirconia containing yttrium oxide in general. Moreover, there remains a potential problem of decreased oxygen ion conductivity due to inclusion of zirconia grains having a monoclinic system.

SUMMARY OF THE INVENTION

According to the present invention, there is provided partially stabilized zirconia comprising yttrium oxide; an MgO ingredient in the grain boundary; and the remainder being zirconium oxide and unavoidable impurities.

Preferably a critical temperature difference of the partially stabilized zirconia is larger than or equal to 340° C.

According to one aspect of the present invention, there is provided partially stabilized zirconia, comprising 1.5–7.0% by mole of a stabilizer wherein more than 70% by mole of the stabilizer is yttrium oxide, and the remainder is at least one compound selected from the group consisting of ytterbium oxide, calcium oxide, and cerium oxide; an MgO ingredient; and the remainder being zirconium oxide and unavoidable impurities, wherein a critical temperature difference of the partially stabilized zirconia is larger than 330° C.

According to another aspect of the present invention, there is provided partially stabilized zirconia comprising 1.5–7.0% by mole of a stabilizer, wherein more than 70% by mole of the stabilizer is yttrium oxide, and the remainder is at least one compound selected from the group consisting of ytterbium oxide, calcium oxide, and cerium oxide; the remainder being zirconium oxide and unavoidable impurities, 0.01–2.0% by weight of a MgO ingredient based on the sum of the zirconium oxide and the stabilizer; 0.1–30% by weight of a $Al_2O_3$ ingredient based on the sum of the zirconium oxide and the stabilizer; and 0.3–3.0% by weight of a $SiO_2$ ingredient based on the sum of the zirconium oxide and the stabilizer; wherein a critical temperature difference of the partially stabilized zirconia is larger than or equal to 340° C.

Further, in the present invention, the partially stabilized zirconia may be suitably used as a solid electrolyte body in an electrochemical device with a pair of electrodes in contact with a surface of the solid electrolyte body.

DESCRIPTION OF TIM PREFERRED EMBODIMENT

Figure 1:
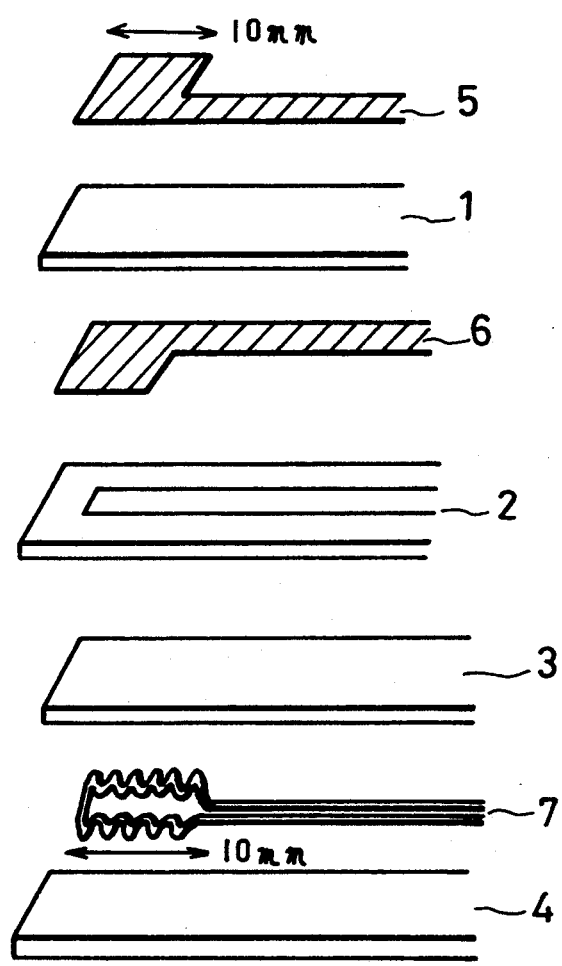
FIG. 1 shows each sheet of a laminated structure of a planar oxygen sensor device with an integrated heater.

One aspect of the present invention is partially stabilized zirconia containing yttrium oxide as a stabilizer, and having a grain boundary containing an MgO ingredient, or combining an MgO, an $Al_2O_3$, and an $SiO_2$ ingredient. The partially stabilized zirconia according to the present invention characteristically has excellent thermal shock resistance. Another aspect of the present invention is an electrochemical device having this partially stabilized zirconia as a solid electrolyte body, the device also having excellent thermal shock resistance.

The terminology "zirconia ceramics" is interchangeably used in this specification to refer to partially stabilized zirconia containing yttrium oxide.

To prepare partially stabilized zirconia according to the present invention, precursors of an MgO, an $Al_2O_3$, and/or an $SiO_2$ ingredient are added as sintering aids, and these ingredients are considered to be present in the grain boundary according to results of an X-ray microanalyzer. These ingredients are believed to lead to excellent thermal shock resistance of zirconia ceramics expressed in terms of a critical temperature difference.

Precursors of MgO, $Al_2O_3$, and $SiO_2$ ingredients give glass with a glass transition temperature lower than a sintering temperature. The glass is believed to be present in the grain boundary and on the outer surfaces of partially stabilized zirconia. The glass is efficiently dispersed to decrease micropores in zirconia ceramics to improve thermal shock resistance. Moreover, since the glass covers the surface of zirconia ceramics and grains, thermal stability of grains belonging to a tetragonal system is assumed to be enhanced. When the content of an $SiO_2$ ingredient is limited compared to that of an MgO and an $Al_2O_3$ ingredient, it is possible that a small amount of $MgAl_2O_4$ in spinel structure Forms simultaneously.

A sintering temperature of zirconia ceramics favorably decreases due to the addition of sintering aids. The lower sintering temperature or better sintering ability helps reduce the size of grains in zirconia ceramics and gives high density and high mechanical strength. Moreover, since grains belonging to a tetragonal system are kept small by the lower sintering temperature, thermal stability related to the possible phase transition of zirconia ceramics improves. Furthermore, the lower sintering temperature leads to more facile activation of electrodes in an electrochemical device using the zirconia ceramics as a solid electrolyte body, and thus the device operates better at lower temperatures.

Partially stabilized zirconia containing yttrium oxide as a stabilizer is disclosed below. A favorable molar ratio of stabilizers in partially stabilized zirconia ranges from 1.5% by mole to 7.0% by mole, and the stabilizers are favorably composed of more than 70% by mole of yttrium oxide as a major component. The reminder of the stabilizer can be other commonly used stabilizers, such as ytterbium oxide, calcium oxide, cerium oxide, other rare earth oxides, etc.

Starting materials for zirconia ceramics according to the present invention can be powders of known partially stabilized zirconia containing yttrium oxide, or powders of its precursors, i.e., a mixture of appropriate compounds that give partially stabilized zirconia containing yttrium oxide, such as a mixture of zirconium oxide powders and yttrium oxide powders in an appropriate molar ratio. Powders can be prepared by any of the known methods, such as an oxidation method, a coprecipitation method, a thermal decomposition method, alkoxide hydrolysis method, etc.

Powders of such zirconia ceramics precursors preferably have a BET specific surface area ranging from 4 to 20 $m^2/g$. When these precursor powders have a BET specific surface area below 4 $m^2/g$, the sintering ability of a compact made of such powders is not favorable. Moreover, a fired body of such a compact does not give favorable mechanical strength, thermal stability, or thermal shock resistance. When these precursor powders have a BET specific surface area over 20 $m^2/g$, these fine powders tend to condense to result in unreliable repeatability in preparing high density zirconia ceramics. Moreover, such powders are too fine to easily form a compact by green sheet molding and by insert molding. Besides, a resultant compact from such fine powders may not have satisfactory machinability, and a compression ratio upon firing is not reliable.

Starting materials for the stabilizer include not only oxide ingredients themselves, such as yttrium oxide, ytterbium oxide, calcium oxide, and other rare earth oxides, but also other compounds that give appropriate oxides upon heating, such as corresponding carbonates, nitrates, chlorides, acetates, oxalates, etc. When oxide powders are used, those having a BET specific surface area ranging from 4 to 20 $m^2/g$ are preferable, considering the particle sizes of the zirconia ceramics precursors.

When these powders of stabilizer precursors have a BET specific surface area below 4 $m^2/g$, a compact does not have favorable sintering ability, and grains belonging to the tetragonal system in a resultant fired body do not have satisfactory stability. When these powders of stabilizer precursors have a BET specific surface area over 20 $m^2/g$, it becomes more difficult to homogeneously disperse the stabilizer precursors in zirconia ceramics precursors so that it becomes more difficult to reliably obtain desires quality. Besides, all the problems due to fine powders mentioned for zirconia ceramics precursors happen in this case also.

The sintering aids that provide MgO, $Al_2O_3$, and $SiO_2$ ingredients are disclosed below. Obviously MgO powders, $Al_2O_3$ powders, and $SiO_2$ powders can be favorably used as sintering aids. A mixture of these powders is also favorable. Moreover, any compounds that give such oxide ingredients upon heating can be used also. Any of such suitable powders is homogeneously mixed with powders of zirconia ceramics precursors.

Examples of MgO-ingredient precursors, besides magnesium oxide itself, are inorganic salts such as magnesium chloride, magnesium nitrate, magnesium sulfate, and magnesium hydroxide; organic salts such as magnesium acetate, magnesium oxalate; an organometallic compound such as magnesium alkoxide; and a coordination compound such as magnesium acetylacetonate.

Besides $Al_2O_3$ itself in powder or in colloid form, examples of $Al_2O_3$-ingredient precursors that give $Al_2O_3$ upon heating, are inorganic salts of aluminum, organic salts of aluminum, organometallic aluminum compounds, etc.

Powders of polymorphisms of $SiO_2$ such as silica sand, quartz sand, quartz, cristobalite, tridymite, coesite, etc. are favorably used. Zircon ($ZrSiO_4$) powders are also favorable. Examples of $SiO_2$-ingredient precursors that give $SiO_2$ upon heating are colloidal silicate, inorganic salts of silicon, organic salts of silicon, organometallic silicon compounds, etc.

Certain precursors can give two oxide ingredients at the same time. Such precursors include spinel ($MgAl_2O_4$) powders and a mixture of powders that give MgO and $Al_2O_3$ ingredients upon heating. Likewise, possible precursors include talc ($Mg_3(Si_4O_{10})(OH)_2$) powders and a mixture of powders that give MgO and $SiO_2$ ingredients upon heating. Furthermore, precursors that provide $Al_2O_3$ and $SiO_2$ ingredients include compounds that contain both an $SiO_2$ and an $Al_2O_3$ ingredient such as kibushi clay, kaolin ($Al_2O_3.2SiO_2$), mullite ($3Al_2O_3.2SiO_2$). Likewise, a mixture of compounds that give $Al_2O_3$ and $SiO_2$ ingredients upon heating is also used.

Possible precursors to give MgO, $Al_2O_3$, and $SiO_2$ ingredients include powders of cordierite ($2MgO.2Al_2O_3.5SiO_2$), powders of glass belonging to $MgO-Al_2O_3-SiO_2$ system, and a mixture of powders that give MgO, $Al_2O_3$, and $SiO_2$ ingredients upon heating.

A characteristic feature of the present invention is considered that grain boundaries of the zirconia ceramics contain at least an MgO ingredient, and that this structural feature is related to excellent thermal shock resistance in the zirconia ceramics according to the present invention. Preferably grain boundaries contain MgO, $Al_2O_3$, and $SiO_2$ ingredients simultaneously for this purpose.

MgO, $Al_2O_3$, and $SiO_2$ ingredients in zirconia ceramics due to sintering aids are effective in enhancing the sintering ability of a compact in which its sintering temperature is decreased. Therefore, thermal shock resistance, mechanical strength, and thermal stability of the resultant zirconia ceramics improves by these sintering aids.

Amounts of sintering aids that give the three ingredients are appropriately chosen in certain ranges, considering the types of starting powders and required properties for the zirconia ceramics.

A favorable content of an MgO ingredient in the partially stabilized zirconia ranges from about 0.01 to about 2.0%, preferably from about 0.05 to about 1.0% by weight based on the sum of zirconium oxide and the stabilizers without a sintering aid. When a content of an MgO ingredient is less than 0.01% by weight, thermal shock resistance of the zirconia ceramics is not satisfactory. On the other hand when a content of an MgO ingredient is more than 2.0% by weight, such properties as mechanical strength and electrical properties of the zirconia ceramics are not satisfactory.

A favorable content of an $Al_2O_3$ ingredient in partially stabilized zirconia ranges from about 0.1 to about 30%, preferably about 0.1 to about 3.0%, due to sintering ability, by weight based on the sum of zirconium oxide and the stabilizers without a sintering aid. When a content of an $Al_2O_3$ ingredient is less than 0.1%, the MgO ingredient is not dispersed by the formation of glass belonging to an $MgO-Al_2O_3-SiO_2$ system; and mechanical strength and thermal stability of the zirconia ceramics due to a decrease in micropores are not observed. On the other hand when a content of an $Al_2O_3$ ingredient is more than 30% by weight, unfavorable properties in the zirconia ceramics result: electrical properties and mechanical strength deteriorate due to inferior sintering ability.

A favorable content of an $SiO_2$ ingredient in partially stabilized zirconia ranges from about 0.3 to about 3.0%, preferably about 0.3 to about 1.5%, by weight based on the sum of zirconium oxide and the stabilizers without a sintering aid. When an content of a $SiO_2$ ingredient is less than 0.3% by weight, thermal stability relating to the possible phase transition of grains belonging to the tetragonal system in the zirconia ceramics is presumed to be unsatisfactory because of a limited amount of compounds in an $MgO-Al_2O_3-SiO_2$ system; the vitreous compounds cannot cover over surfaces of grains belonging to the tetragonal system. On the other hand when a content of an $SiO_2$ ingredient is more than 3% by weight, thermal shock resistance of the zirconia ceramics tends to deteriorate.

To obtain zirconia ceramics according to the present invention, first, to powders of zirconia ceramics or powders of its precursors are added powders of sintering aids to provide an MgO ingredient and, optionally, powders of sintering aids to provide $Al_2O_3$ and/or $SiO_2$ ingredients. Then the resultant mixture is mixed by dry grinding and/or wet grinding to give a uniform mixture.

A sintering aid that provides MgO, $Al_2O_3$, and $SiO_2$ ingredients can be added independently or in a combined form to powders of partially stabilized zirconia or its precursors. To mix and combine sintering aids, they are chemically mixed together by a coprecipitation method or a hydrolysis method, then the resultant mixture is calcined, followed by grinding to give a homogeneous mixture.

To obtain zirconia ceramics according to the present invention, it is important to homogeneously disperse the stabilizers and the sintering aids. For this purpose it is favorable to introduce a mixing process in manufacturing the zirconia ceramics in which powders undergo wet grinding with an appropriate medium such as water and/or organic solvents. The uniform mixture thus obtained is dried, calcined, and then ground.

The ground mixture thus obtained is shaped into a compact with a desired shape by press forming, injection molding, green sheet molding, slip casting or any other appropriate forming method.

Finally, the compact is fired by a known method. Typically, a compact is heated at a temperature between about 1250° C. to about 1400° C. for a few hours in air. When a sintering temperature is higher than about 1500° C., an MgO ingredient forms a solid solution in the grains and may not be present in the grain boundary. Moreover, in this firing condition mechanical strength of the resulting zirconia ceramics and thermal stability related to the phase transition of grains belonging to a tetragonal system deteriorate due to grain growth. Therefore, the sintering temperature is preferably lower than about 1400° C.

It was confirmed by X-ray microanalysis that an MgO, an $Al_2O_3$, and an $SiO_2$ ingredient are each present in the grain boundary in the zirconia ceramics according to the present invention. For example, each of an MgO, an $Al_2O_3$, and an $SiO_2$ ingredient is homogeneously dispersed in the grain boundary of partially stabilized zirconia containing 0.68% by weight of an Al₂O₃ ingredient, 0.8% by weight of an SiO₂ ingredient, and 0.5% by weight of an MgO ingredient, all of which were based on the sum of ZrO₂ and the stabilizers without sintering aids.

As a comparative example, neither an Al₂O₃ nor an SiO₂ ingredient is satisfactorily dispersed in the grain boundary of partially stabilized zirconia containing 0.68% by weight of an Al₂O₃ ingredient and 0.8% by weight of an SiO₂ ingredient, without an MgO ingredient, both of which are based on the sum of ZrO₂ and the stabilizers without sintering aids.

Comparing the two cases with and without an MgO ingredient, the presence of an MgO ingredient significantly enhances dispersion of Al₂O₃ and SiO₂ ingredients.

Moreover, the lattice constants of partially stabilized zirconia with an MgO ingredient, shown by X-ray diffraction analysis on its specular glossy surface, are the same as that without a MgO ingredient. This result clearly shows that an MgO ingredient does not dissolve in grains, which would change lattice constants, and is consistent with the data that an MgO ingredient is present in the grain boundary.

An average dimension of grains in the zirconia ceramics according to the present invention is favorably equal to or smaller than about 2 μm due to mechanical strength and thermal stability relating to the possible phase transition. Grains are preferably crystalline. Most of the grains preferably belong to a tetragonal system or belong to the tetragonal system and the cubic system.

Partially stabilized zirconia containing yttrium oxide according to the present invention has satisfactory, improved thermal shock resistance expressed by a critical temperature difference which is obtained by dispersing an MgO ingredient in the grain boundary.

Partially stabilized zirconia containing yttrium oxide according to the present invention has improved sintering ability due to homogeneous dispersion of MgO, Al₂O₃, and SiO₂ ingredients. The decrease in the sintering temperature is related to making zirconia grains in a tetragonal system small without further grain growth, and a phase transition from the tetragonal system to a monoclinic system is prevented resulting in better thermal stability. A glass layer formed due to the addition of 0.3% by weight of SiO₂ or its precursors, covers the zirconia ceramics and zirconia grains to prevent water vapor from contacting them. An electrochemical device according to the present invention has improved thermal shock resistance because of the application of partially stabilized zirconia containing yttrium oxide as a solid electrolyte body.

EXAMPLES

The present invention is disclosed below more in detail but it shall not be limited to the following examples.

(Example 1)

Twelve runs from No. 1 to No. 12 were performed with various amounts of Al₂O₃ powders, SiO₂ powders, and MgO powders as well as various sintering temperatures, and these variables are shown in Table 1. The other experimental conditions of these twelve runs are kept the same.

To water were added ZrO₂ powders in an amount of 96 parts by mole having an average particle size of about 2 μm and a BET specific surface area of 7 m²/g, Y₂O₃ powders in an amount of 4 parts by mole having an average particle size of about 1 μm and a BET specific surface area of 10 m²/g, kaolin powders having an average particle size of about 2 μm which essentially consist of 46% by weight of Al₂O₃ and 54% by weight of SiO₂, and MgCO₃ (magnesite) powders having an average particle size of about 2 μm.

Then these powders in the water were mixed and dispersed for two hours in a ball mill with a ZrO₂ ball to give a slurry. The slurry obtained was dried and then calcined product at about 600° C. for two hours. The calcined underwent dry grinding for 48 hours in a ball mill with a ZrO₂ ball. The ground powders were passed through sieves.

To the ground powder thus obtained in 100 parts by weight were added poly(vinyl alcohol) in 0.2 parts by weight in water to give a slurry. The slurry obtained was treated with a spray dryer method to give powders with 80 mesh pass.

These powders were shaped in a mould by pressing at 500 kgf/cm², and then by isostatic pressing at 1000 kgf/cm² to give a compact. The compact thus obtained was fired for three hours at a maximum temperature in air shown in Table 1 to give partially stabilized zirconia excelling in thermal shock resistance.

(Evaluation)

A relative density of zirconia ceramics is given by a formula below;

$$\text{relative density (\%)} = \frac{\text{bulk density}}{\text{theoretical density}} \times 100$$

A theoretical density was calculated based on the following assumptions: the density of zirconia ceramics that contains 4% by mole of Y₂O₃, the remainder being ZrO₂, is taken as 6.00 g/cm³; the density of Al₂O₃, SiO₂, and MgO are taken as 3.97, 2.60, and 3.65 g/cm³, respectively.

Mechanical strength and thermal shock resistance of the partially stabilized zirconia were evaluated as disclosed below.

Mechanical strength was measured by a rectangular bar of 40 mm (length)×4.0 mm (width)×3.0 mm (height) with the six principal faces treated by a diamond wheel #800. Two adjacent, parallel edges of 40 mm in the bar had chamfers with their width of 0.1 to 0.2 mm by a diamond wheel #1200.

First, for the evaluation of mechanical strength, ten samples underwent a four-point bending strength test specified in Japan Industrial Standard (JIS) R-1601-1981 with an outside span of 30 mm, an inside span of 10 mm, and a cross head speed of 0.5 mm/min; each rectangular bar was placed on two rods such that the largest face having the two chamfered edges contacts the rods. Then the ten samples were held at 250° C. for two hours under a pressure of 40 kgf/cm² in an autoclave. Finally the 10 samples underwent the same bending strength test. The mechanical strength before and after the autoclave treatment was tabulated in Table 1.

A thermal-shock-resistance test was performed on a rectangular bar of 10 mm(length)×3.2 mm (width)×1.0 mm (height) with the six principal faces treated by a diamond wheel #800. All the edges in the bar had chamfers with a width of about 0.1 mm by a diamond wheel #1200.

20 samples were heated in an electric furnace to 200° C. and a temperature of each of them was further measured by a thermocouple. Then the 20 hot samples were quenched by immersing them in water at 15° C. Finally the presence of cracks in each sample was examined through a microscope with the expansion of about 40 times.

Then this heating and quenching cycle was repeated such that each of the 20 samples was heated to a temperature higher by 20° C. from that in the previous cycle until the temperature reached a critical point in which half, i.e. 10, of the tested samples had cracks. The temperature difference between the critical temperature and the water temperature of 15° C. was taken as a critical temperature difference of a $\Delta Tc$ (° C.). These results are shown in Table 1.

(Example 2)

Six runs from No. 13 to No. 17 were performed with various amounts of $Al_2O_3$ powders and various sintering temperatures, as shown in Table 1. The other experimental conditions of these six runs are kept the same. In contrast to the twelve runs in Example 1, contents of both $SiO_2$ and MgO ingredients in these six runs in Example 2 are kept constant.

In Example 1 kaolin powders were used as precursors of $Al_2O_3$ and $SiO_2$ ingredients. In contrast, in Example 2 $Al_2O_3$ powders having an average particle size of about 2 $\mu$m and $ZrSiO_4$ powders having an average particle size of about 2 $\mu$m were used as precursors of $Al_2O_3$ and $SiO_2$ ingredients. A zirconia ceramics was prepared in which the rest of the conditions were the same as Example 1.

Thermal shock resistance and mechanical strength of zirconia ceramics obtained were evaluated in the same manners as in Example 1. These results are shown in Table 1.

(Example 3)

Five runs from No. 18 to No. 22 were performed with various contents of an MgO ingredient and various sintering temperatures, as shown in Table 1. The other experimental conditions of these five runs are kept the same. In contrast to Example 1 and 2, neither an $Al_2O_3$ nor an $SiO_2$ powder is used in Example 3.

A zirconia ceramics was prepared in the same manner as in Example 1 without kaolin powders or other precursors of a $SiO_2$ and an $Al_2O_3$ ingredient.

Thermal shock resistance and mechanical strength of zirconia ceramics obtained were evaluated in the same manners as in Example 1. These results are shown in Table 1.

(Comparative Example 1)

Four runs from No. 23 to No. 26 were performed with various contents of $Al_2O_3$ and $SiO_2$ ingredients as well as various sintering temperatures, as shown in Table 1. In contrast to Examples 1–3 with a total of the 22 runs, none of MgO precursors was used in these four runs. A zirconia ceramics was prepared in the same manner as in Example 1.

Thermal shock resistance and mechanical strength of zirconia ceramics obtained were evaluated in the same manners as in Example 1. These results are shown in Table 1.

(Comparative Example 2)

A zirconia ceramics was prepared in the same manner as in Example 1 except with the absence of sintering aides in these runs in Comparative Example 2.

Thermal shock resistance and mechanical strength of zirconia ceramics obtained were evaluated in the same manners as in Example 1. These results are shown in Table 1.

TABLE 1

| No | $Al_2O_3$ contents | $SiO_2$ contents | MgO contents | Ts (°C.) | Four-point bending strength (n = 10) kgf/mm² First stage (Before autoclave) | After autoclave | $\Delta Tc$ (°C.) | * Evaluations | Remarks |
|---|---|---|---|---|---|---|---|---|---|
| | | | | Embodiment 1 | | | | | |
| 1 | 0.17% | 0.2% | 0.1% | 1325 | 90 | 70 | 430 | A | x |
| 2 | 0.34% | 0.4% | 0.005% | 1350 | 86 | 83 | 340 | B | |
| 3 | 0.34% | 0.4% | 0.01% | 1325 | 90 | 88 | 440 | A | |
| 4 | 0.34% | 0.4% | 0.1% | 1300 | 98 | 98 | 470 | A | |
| 5 | 0.34% | 0.4% | 1.0% | 1275 | 92 | 91 | 450 | A | |
| 6 | 0.34% | 0.4% | 5.0% | 1275 | 70 | 68 | 380 | A | y |
| 7 | 0.68% | 0.8% | 0.005% | 1325 | 86 | 84 | 340 | B | |
| 8 | 0.68% | 0.8% | 0.01% | 1300 | 91 | 89 | 420 | A | |
| 9 | 0.68% | 0.8% | 0.1% | 1275 | 97 | 95 | 430 | A | |
| 10 | 0.68% | 0.8% | 1.0% | 1250 | 96 | 96 | 420 | A | |
| 11 | 0.68% | 0.8% | 5.0% | 1250 | 72 | 66 | 360 | A | y |
| 12 | 3.4% | 4.0% | 0.1% | 1325 | 70 | 68 | 340 | B | y |
| | | | | Embodiment 2 | | | | | |
| 13 | 0.05% | 0.4% | 0.1% | 1350 | 85 | 68 | 400 | A | x |
| 14 | 0.5% | 0.4% | 0.1% | 1300 | 96 | 95 | 460 | A | |
| 15 | 3.0% | 0.4% | 0.1% | 1325 | 95 | 93 | 460 | A | |
| 16 | 10% | 0.4% | 0.1% | 1425 | 93 | 92 | 450 | A | |
| 17 | 40% | 0.4% | 0.1% | 1600 | 71 | 64 | 390 | A | y |
| | | | | Embodiment 3 | | | | | |
| 18 | — | — | 0.005% | 1400 | 82 | 60 | 340 | B | x |
| 19 | — | — | 0.01% | 1375 | 90 | 65 | 370 | A | x |
| 20 | — | — | 0.1% | 1350 | 89 | 65 | 390 | A | x |
| 21 | — | — | 1.0% | 1350 | 91 | 66 | 380 | A | x |
| 22 | — | — | 5.0% | 1350 | 70 | 58 | 340 | B | xy |
| | | | | Comparative example 1 | | | | | |
| 23 | 0.34% | 0.4% | — | 1375 | 82 | 75 | 310 | F | |

TABLE 1-continued

| No | $Al_2O_3$ contents | $SiO_2$ contents | MgO contents | Ts (°C.) | Four-point bending strength (n = 10) kgf/mm² | | ΔTc (°C.) | *Evaluations | Remarks |
|---|---|---|---|---|---|---|---|---|---|
| | | | | | First stage (Before autoclave) | After autoclave | | | |
| 24 | 0.68% | 0.8% | — | 1350 | 84 | 82 | 320 | F | |
| 25 | 1.36% | 1.6% | — | 1350 | 78 | 76 | 300 | F | |
| 26 | 3.4% | 4.0% | — | 1400 | 62 | 60 | 280 | F | |
| Comparative example 2 | | | | | | | | | |
| 27 | — | — | — | 1500 | 80 | 52 | 270 | F | |

*Evaluations were made only about ΔTc. ΔTc > 340° C. is considered to be excellent-A; ΔTc = 340° C. is good-B; ΔTc < 340° C. is failure-F.
x: Bending strength after autoclave in condition of a pressure of 40 kg/cm² at 250° C. for two hours was not satisfactory.
y: Bending strength before autoclave was not satisfactory.

The effect of the presence of an MgO ingredient on a sintering temperature and a critical temperature difference, ΔTc. of resultant zirconia ceramics is shown by the comparison of Example 3 with a MgO ingredient with Comparative Example 2 without any sintering aid. A sintering temperature of 1500° C. in Comparative Example 2 decreases to those ranging from 1350° C. to 1400° C. in the five runs in Example 3. Likewise, a ΔTc of 270° C. in Comparative Example 2 significantly increases to that ranging from 340 ° C. to 390° C. in Example 3.

The presence of $Al_2O_3$ and $SiO_2$ ingredients in addition to an MgO ingredient, as shown in Example 1, further decreases sintering temperatures. For example, run Nos. 10 and 11 in Example 1 gave a sintering temperature as low as 1250° C. Likewise, the increase in ΔTc due to the presence of the three oxide ingredients is clearly shown in Example 1 also; for example, ΔTc reached to as high as 470° C. in run No. 4.

The effect of the presence of an MgO ingredient is further exemplified by comparison of Example 1 in which $Al_2O_3$, $SiO_2$, and MgO ingredients are present with Comparative Example 1 in which only an $Al_2O_3$ and a $SiO_2$ ingredients are present without an MgO ingredient. It should be noted that contents of $Al_2O_3$ and $SiO_2$ ingredients in run Nos. 2–6 in Example 1 are the same as those in run No. 23 in Comparative Example 1.

Run Nos. 2–6 in Example 1 with an MgO ingredient had sintering temperatures ranging from 1275° C. to 1350° C., and these temperatures show improvement from a sintering temperature of 1375° C. in run No. 23 in Comparative Example 1. Likewise, a ΔTc ranging from 340° C. to 470° C. in runs No. 2–6 in Example 1 is much better than that of 310° C. in run No. 23.

The five runs in Example 1 further show a lower threshold of an MgO ingredient content of 0.01% by weight. A ΔTc of 340° C. observed in run No. 2 with an MgO ingredient content of 0.005% by weight below the threshold drastically increases to 440° C. with a MgO ingredient of 0.01% by weight on the threshold.

(Example 4)

To an aqueous solution of $Y(NO_3)_3$ that contains 6.2 parts by mole of $Y(NO_3)_3$, were added 93.8 parts by mole of $ZrO_2$ powders having an average particle size of about 2 μm and a BET specific surface area of 7 m²/g, kibushi clay having an average particle size of 2 μm that contains 30% by weight of $Al_2O_3$ and 53% by weight of $SiO_2$, and MgO powders having an average particle size of about 1 μm. The added amount of the kibushi clay and the MgO powders are 1.0% and 0.2% by weight, respectively, based on the sum of the $ZrO_2$ powders and the calculated amount of $Y_2O_3$ to be given. This ratio of $ZrO_2$ and $Y(NO_3)_3$ corresponds to 96.8 parts by mole of $ZrO_2$ to 3.2 parts by mole of $Y_2O_3$.

Then these powders in the aqueous solution were mixed and dispersed for two hours in a ball mill with a $ZrO_2$ ball to give a slurry. The slurry obtained was dried and then calcined product at about 1000° C. for two hours. The calcined underwent dry grinding for 40 hours in a ball mill with a $ZrO_2$ ball to give ground powders. The ground powders were screened through sieves with 60 meshes.

To 100 parts by weight of the ground powders thus obtained were added 8 parts by weight of poly(vinyl butyral), 5 parts by weight of dioctyl phthalate, 35 parts by weight of toluene as solvent, and 35 parts by weight of 2-propanol as another solvent, and the mixture was mixed for 15 hours in a ball mill with a $ZrO_2$ ball to give a slurry. The slurry was passed through a sieve with 80 meshes, and its viscosity was adjusted to 20,000 cps.

The slurry thus obtained was shaped by a doctor blade process, and then dried at 100° C. for three hours to give a green sheet with a thickness of 500 μm. A few more sheets were laminated on the first one by the same doctor blade process, and the laminated sheets were fired at 1350° C. for three hours to give zirconia ceramics with a relative density of 98%. Mechanical strength and thermal shock resistance of the zirconia ceramics were evaluated in the same manner as Example 1.

A sample gave an initial strength of 120 kgf/mm² by a four-point bending strength test. After it was kept at 250 ° C. for two hours in an autoclave, the resultant sample gave a strength of 114 kgf/mm² by the bending strength test. A critical temperature difference ΔTc by the thermal shock resistance test was found to be 480° C.

(Example 5)

FIG. 1 shows each sheet of a laminated structure of a planar oxygen sensor device with an integrated heater. A solid electrolyte body 1, an air-introducing sheet 2, a sealing sheet 3, and a heater sheet 4 were made of the green sheets of zirconia ceramics by the method disclosed in Example 4. Each of the solid electrolyte body 1, the air-introducing sheet 2, the sealing sheet 3, and the heater sheet 4, had a size of 64 mm (length)×4 mm (width)×0.4 mm (height).

A measuring electrode 5 and a reference electrode 6 were connected to the top and the bottom surfaces of the solid electrolyte body 1, respectively. Both of the electrodes 5 and 6 were made of a cermet of Pt and $ZrO_2$. The heater was made of a cermet of Pt and $Al_2O_3$.

To compare the effects of the presence of an MgO ingredient in zirconia ceramics in the oxygen sensor, another planar oxygen sensor device with an integrated heater having the same structure as the device above was made of green sheets of zirconia ceramics without an MgO ingredient.

A thermal-shock-resistance test was performed on ten devices according to the present invention and ten comparative devices. The test is as follow: first the heater 7 in a device was provided with electricity generating four watts for five minutes to heat the device; then the heated device was submerged into water; finally the presence of cracks in the device was examined by a microscope with the magnification of 40 times.

Ten devices according to the present invention did not give any cracks. In contrast seven out of ten comparative devices had cracks. Clearly thermal shock resistance of the device according to the present invention drastically improves due to the presence of an MgO ingredient in the green sheets of zirconia ceramics.

What is claimed is:

1. A sintered zirconia ceramic, consisting essentially of:
   (a) grains of partially stabilized zirconia consisting essentially of:
       (i) 1.5–7.0% by mole of a stabilizer, wherein more than 70% by mole of said stabilizer is yttrium oxide, and
       (ii) as the remainder, zirconium oxide and unavoidable impurities; and
   (b) grain boundaries including a glass phase containing:
       (i) 0.01–2.0% by weight of MgO based on the sum of said zirconium oxide and said stabilizer;
       (ii) 0.1–30% by weight of $Al_2O_3$ based on the sum of said zirconium oxide and said stabilizer; and
       (iii) 0.3–3.0% by weight of $SiO_2$ based on the sum of said zirconium oxide and said stabilizer,
   wherein a critical temperature difference of said sintered zirconia ceramic is larger than or equal to 340° C.

2. A sintered zirconia ceramic as defined in claim 1, wherein said sintered zirconia ceramic is prepared by a step of sintering a compacted body of a powder of starting materials at a temperature ranging from 1,250° C. to 1,350° C.

3. A sintered zirconia ceramic as defined in claim 1, wherein 0.3–1.5% by weight of $SiO_2$ is present in grain boundaries based on the sum of said zirconium oxide and said stabilizer.

4. A sintered zirconia ceramic as defined in claim 3, wherein 0.3–0.8% by weight of $SiO_2$ is present in grain boundaries based on the sum of said zirconium oxide and said stabilizer.

5. A sintered zirconia ceramic as defined in claim 3, wherein a critical temperature difference of said sintered zirconia ceramic is larger than or equal to 420° C.

6. A sintered zirconia ceramic as defined in claim 1, wherein 0.05–1.0% by weight of MgO is present in grain boundaries based on the sum of said zirconium oxide and said stabilizer.

7. A sintered zirconia ceramic as defined in claim 1, wherein 0.1–3.0% by weight of $Al_2O_3$ is present in grain boundaries based on the sum of said zirconium oxide and said stabilizer.

8. An electrochemical device, comprising:
   a solid electrolyte body, consisting essentially of:
       grains of partially stabilized zirconia consisting essentially of 1.5–7.0% by mole of a stabilizer, wherein more than 70% by mole of said stabilizer is yttrium oxide, the remainder being zirconium oxide and unavoidable impurities; and
       grain boundaries including a glass phase containing: 0.01–2.0% by weight of MgO based on the sum of said zirconium oxide and said stabilizer; 0.1–30% by weight of $Al_2O_3$ based on the sum of said zirconium oxide and said stabilizer; and 0.3–3.0% by weight of $SiO_2$ based on the sum of said zirconium oxide and said stabilizer,
   wherein a critical temperature difference of said solid electrolyte body is larger than or equal to 340° C.; and
   a pair of electrodes in contact with a surface of said solid electrolyte body.

9. An electrochemical device as defined in claim 8, wherein said solid electrolyte body is prepared by a step of sintering a compacted body of a powder of starting materials at a temperature ranging from 1,250° C. to 1,350° C.

10. An electrochemical device as defined in claim 8, wherein 0.3–1.5% by weight of $SiO_2$ is present in grain boundaries based on the sum of said zirconium oxide and said stabilizer.

11. An electrochemical device as defined in claim 10, wherein 0.3–0.8% by weight of $SiO_2$ is present in grain boundaries based on the sum of said zirconium oxide and said stabilizer.

12. An electrochemical device as defined in claim 10, wherein a critical temperature difference of said sintered zirconia ceramic is larger than or equal to 420° C.

13. An electrochemical device as defined in claim 8, wherein 0.05–1.0% by weight of MgO is present in grain boundaries based on the sum of said zirconium oxide and said stabilizer.

14. An electrochemical device as defined in claim 8, wherein 0.1–3.0% by weight of $Al_2O_3$ is present in grain boundaries based on the sum of said zirconium oxide and said stabilizer.

* * * * *